(12) United States Patent
Segall et al.

(10) Patent No.: US 6,589,223 B1
(45) Date of Patent: Jul. 8, 2003

(54) METHOD AND COMPOSITIONS FOR USE IN PERFUSION APPLICATIONS

(75) Inventors: Paul E. Segall, Berkeley, CA (US); Harold D. Waitz, Berkeley, CA (US); Hal Sternberg, Berkeley, CA (US)

(73) Assignee: BioTime, Inc., Berkeley, CA (US)

( * ) Notice: Subject to any disclaimer, the term of this patent is extended or adjusted under 35 U.S.C. 154(b) by 0 days.

(21) Appl. No.: 09/243,921

(22) Filed: Feb. 3, 1999

(51) Int. Cl.[7] ............................................. A61M 31/00
(52) U.S. Cl. ...................................... 604/500; 435/1.2
(58) Field of Search ............................ 604/4.01, 27–29, 604/500, 506, 508, 522; 606/20, 21; 435/1.2

(56) References Cited

U.S. PATENT DOCUMENTS

| | | | |
|---|---|---|---|
| 4,923,442 A | * 5/1990 | Segall et al. ................ 604/522 |
| 5,130,230 A | * 7/1992 | Segall et al. ................ 604/4.01 |
| RE34,077 E | * 9/1992 | Segall et al. ................ 604/507 |
| 5,405,742 A | * 4/1995 | Taylor ........................ 435/1.2 |
| 5,514,536 A | * 5/1996 | Taylor ........................ 435/1.2 |
| 5,574,019 A | 11/1996 | Segall et al. | |
| 5,613,944 A | 3/1997 | Segall et al. | |
| 5,730,720 A | 3/1998 | Sites et al. | |
| 5,968,726 A | 10/1999 | Segall et al. | |
| 6,080,538 A | * 6/2000 | Segall et al. ................ 604/500 |
| 6,218,099 B1 | * 4/2001 | Segall et al. ................ 435/1.2 |

* cited by examiner

*Primary Examiner*—Manuel Mendez
*Assistant Examiner*—Michael M. Thompson
(74) *Attorney, Agent, or Firm*—Bret E. Field.; Bozicevic, Field & Francis

(57) ABSTRACT

Methods and compositions for use in perfusion applications are provided. In the subject methods, a subject or derivative thereof, e.g. isolated organ or tissue, is infused, perfused and/or transfused with at least two fluid compositions. The first fluid composition is a non-naturally occurring biological buffer free plasma-like solution and the second fluid composition is a fluid blood composition. In a preferred embodiment, an additional volume of the first solution, or a derivative thereof, is administered to the patient following introduction of the fluid blood composition. Also provided are kits and systems for performing the subject methods. The subject methods and compositions find use in variety of perfusion applications, including the treatment of hypothermic surgical applications, cryogenic procedures, and the like.

11 Claims, No Drawings

METHOD AND COMPOSITIONS FOR USE IN PERFUSION APPLICATIONS

TECHNICAL FIELD

The technical field of this invention is plasma substitute solutions and their use in perfusion applications.

BACKGROUND OF THE INVENTION

Perfusion, in which a fluid is introduced and moved through a tissue or organ, e.g. via the circulatory system, plays a prominent role in many medical applications. Such applications include treatments for blood lost during surgery or trauma, or when a tissue, organ, group of organs or an entire subject needs to be maintained at a hypothermic or frozen state. Such applications also include applications in which a patient's blood is flowed through an external device, such as a cardiopulmonary bypass machine, where the extra circulatory volume space resulting from attachment of the patient's circulatory system to the device must be filled with a compatible blood substitute, i.e. blood volume expander.

Fluids that are employed in the majority of perfusion applications are physiologically acceptable. The first physiologically acceptable solutions employed for perfusion applications were derived from mammalian blood. Although such solutions have been used with success, because such solutions are derived from natural blood, they can contain various pathogenic substances, such as viral pathogens such as HIV, Hepatitis B, and other pathogens, e.g. prions such as those associated with Cruetzfeldt-Jakob disease, and the like. Disadvantages associated with the use of such solutions include the need for donors and the requirement to perform expensive screening tests to identity pathogenic agents. As such, use of blood substitute and plasma substitute solutions derived from natural blood are not free of complication.

Accordingly, a variety of synthetic blood and plasma substitute solutions have been developed which are prepared from non-blood derived components. Although synthetic plasma-like solutions have found increasing use in a variety of applications, no single solution has proved suitable for use in all potential applications.

Therefore, there is continued interest in the development of new methods of perfusion, as well as solutions for use therein.

Relevant Literature

Various physiologically acceptable solutions, particularly blood substitute solutions, and methods for their use are described in U.S. Pat. Nos.: RE 34,077; 3,677,024; 3,937,821; 4,001,401; 4,061,736; 4,216,205; 4,663,166; 4,812,310; 4,908,350; 4,923,442; 4,927,806; 5,082,831; 5,084,377; 5,130,230; 5,171,526; 5,210,083; 5,274,001; 5,374,624; and 5,407,428.

Additional references describing physiologically acceptable solutions, including blood substitute solutions include: Bishop et al., Transplantation (1978) 25:235–239; Messmer et al., Characteristics, Effects and Side-Effects of Plasma Substitutes, pp 51–70; Rosenberg, Proc. 12th Congr. Int. Soc. Blood Transf. (1969); Spahn, Anesth. Analg. (1994) 78:1000–1021; Biomedical Advances In Aging (1990) (Plenum Press) Chapter 19; Wagner et al., Clin. Pharm. (1993) 12:335; ATCC Catalogue of Bacteria & Bacteriophages (1992) p 486; and 06-3874-R8-Rev. May (1987) Abbott Laboratories, North Chicago, Ill. 60064, USA.

Additional references describing various applications of such solutions, including hypothermic applications, include: Bailes et al., Cryobiology (1990) 27:615–696(pp 622–623); Belzer et al., Transplantation (1985) 39:118–121; Collins, Transplantation Proceedings (1977) 9:1529; Fischer et al., Transplantation (1985) 39:122; Kallerhoff et al., Transplantation (1985) 39:485; Leavitt et al., FASB J. (1990) 4: A963; Ross et al., Transplantation (1976) 21:498; Segall et al. FASB J. (1991) 5: A396; Smith, Proc. Royal Soc. (1956) 145: 395; Waitz et al., FASB J. (1991) 5.

Lehninger, Biochemistry ($2^{nd}$ Ed., 1975), pp 829ff provides a review of blood and its constituents.

SUMMARY OF THE INVENTION

Methods and compositions are provided for use in perfusion applications. In the subject methods, a subject (e.g. an organism or derivative thereof, such as an organ or tissue) is sequentially perfused with at least one quantity of a plasma-like solution and at least one quantity of a fluid blood composition. In one preferred embodiment, the subject is then perfused with at least one additional quantity of the plasma-like solution. The plasma-like solution is a non-naturally occurring solution that at least includes electrolytes, an oncotic agent and a dynamic buffering system. The fluid blood composition is a fluid composition derived from whole blood and generally comprises: red blood cells, whole plasma or fractions thereof, whole blood, etc. Also provided are kits and systems for use in performing the subject methods. The subject methods and compositions find use in a variety of different applications, including the treatment of hypovolemic subjects, in regional chemotherapy, in cryogenic preservation, and the like.

DESCRIPTION OF THE SPECIFIC EMBODIMENTS

Methods and compositions for use in the perfusion of a subject are provided. In the subject methods, at least a plasma-like solution and fluid blood composition are sequentially introduced into the circulatory system of a subject. In a preferred embodiment, the subject is then perfused with an additional volume of plasma-like solution. The plasma-like solution is a non-naturally occurring solution comprising at least electrolytes, an oncotic agent and a dynamic buffering system. The fluid blood composition is whole blood or a fluid composition derived from whole blood, such as purified red blood cells, whole plasma or fractions thereof. Also provided are kits and systems for carrying out the subject methods. The subject methods and compositions find use in a variety of different applications, including the treatment of hypovolemic subjects, regional chemotherapy, tissue and organ preservation, and the like. In further describing the subject invention, the subject solutions are detailed first followed by a discussion of the subject methods in which the solutions find use.

Before the subject invention is further described, it is to be understood that the invention is not limited to the particular embodiments of the invention described below, as variations of the particular embodiments maybe made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

FLUID COMPOSITIONS

As mentioned above, a critical aspect of the subject invention is the sequential administration of at least two different types of fluid compositions: (a) a non-naturally occurring plasma-like solution; and (b) a fluid blood composition. The subject methods may further include the administration of one or more additional types of solutions, which solutions are generally derivatives of the non-naturally occurring plasma-like solution. Each of the solutions finding use in the subject invention are described in greater detail below.

Non-Naturally Occurring Plasma-Like Solutions

The subject non-naturally occurring plasma-like solutions are solutions that do not occur in nature, e.g. they are not produced by animals or plants or other organisms. As such, the subject solutions are synthetic in that they are produced through some human interaction or processing, such as purification, separation, genetic engineering, laboratory combination, and the like.

The plasma-like solutions of the subject invention are physiologically acceptable, by which is meant that the solutions may be introduced into the vasculature of a host without inherently causing a toxic reaction. The solutions have a pH ranging from about 4 to 10, usually from about 4.5 to 9 and more usually from about 5 to 8.5.

The solutions comprise a plurality of electrolytes, including: sodium ion, chloride ion, potassium ion and calcium ion, and optionally magnesium ion. The sodium ion concentration of the solutions ranges from about 70 to 160, usually from about 110 to 150, and in some embodiments from 130 to 150 mM. The concentration of chloride ion in the solutions ranges from about 70 to 170, usually from about 80 to 160, more usually from about 100 to 135 and in some embodiments from about 110 to 125 mM. The concentration of potassium ion ranges from the physiological to subphysiological, where by "physiological" is meant from about 3.5 to 5, usually from about 4 to 5 mM, and by "subphysiological" is meant from about 0 to 3.5, usually from about 2 to 3 mM, where in many embodiments of the invention, the amount of potassium ion will range from about 1 to 5, usually from about 2–3 mM, where in certain embodiments, the amount of potassium ion may be higher than 5 mM and range as high as about 5.5 mM or higher, but will usually not exceed about 5.5 mM. The solutions also comprise calcium ion in an amount ranging from about 0.5 to 6.0 mM, and in many embodiments from about 0.5 to 4.0, usually from about 2.0 to 2.5 mM, but in certain embodiments from about 4.0 to 6.0, usually from about 4.5 to 6.0 mM. Optionally, the solutions may further comprise magnesium. When present, the magnesium ion ranges from about 0.01 to 10 mM, usually from about 0.3 to 3.0 and more usually from about 0.3 to 45 mM.

The solutions also comprise a dynamic buffering system, where the term dynamic buffering system is used to refer to one or more reagents that work in combination to keep the pH of the solution in a certain range in an in vivo environment. Preferably, the reagent members of the dynamic buffering system are normal biological components that maintain in vivo biological pH. The dynamic buffering system concept rests on the discovery by the inventors that compounds with no intrinsic buffering capacity in the biological range, such as lactate, acetate, or gluconate which are capable of being metabolized in vivo, act with other solution components to maintain a biologically appropriate pH in an animal, even at hypothermic temperatures and at essentially bloodless conditions. The dynamic buffering system of the present invention depends in part on oxygenation and removal of carbon dioxide ($CO_2$). The dynamic buffer of the invention has no or substantially no ability to act as a buffer outside of a biological system, i.e., a dynamic buffer maintains pH in the biological range in vivo but not in a cell free environment.

A critical component of the dynamic buffering system of the invention is a carboxylic acid, salt or ester thereof. By a carboxylic acid, salt or ester thereof is meant a compound having the general structural formula RCOOX, where R is an alkyl, alkenyl, or aryl, branched or straight chained, containing 1 to 30 carbons which carbons may be substituted, and preferably one of the carbon chains that compose the carbon chain of lactate, acetate, gluconate, citrate, pyruvate, or other biological metabolites; and X is hydrogen or sodium or other biologically compatible ion substituent which can associate at the oxygen position.

The solution of the present invention does not include a conventional biological buffer. By "conventional buffer" is meant a compound which in solution, in vitro, maintains pH at a particular range. By "conventional biological buffer" is meant a compound which in a cell-free system maintains pH in the biological range of 7–8. Examples of conventional biological buffers include N-2-Hydroxyethylpiperazine-N'-2-hydroxypropanesulfonic acid (HEPES), 3-(N-Morpholino)propanesulfonic acid (MOPS), 2-([2-Hydroxy-1,1-bis(hydroxymethyl)ethyl]amino)ethanesulfonic acid (TES), 3-[N-tris(Hydroxy-methyl)ethylamino]-2-hydroxyethyl]-1-piperazinepropanesulfonic acid (EPPS), Tris[hydroxymethyl]-aminomethane (THAM), and Tris[hydroxymethyl]methyl aminomethane (TRIS). Conventional biological buffers have a pK in the physiological range and function most efficiently in this range. Therefore, these buffers function independently of normal biological processes and are most potent in cell-free systems.

The absence of a conventional biological buffer in the solution of the invention confers several important medical advantages. For example, lower concentrations of buffers consisting of normal biological components are required to maintain in vivo pH, compared to conventional biological buffers. Conventional biological buffers may also pose toxicity problems. Further, the absence of a biological buffer allows the solution to be terminally heat sterilized. Generally, medical solutions are preferred to be terminally heat sterilized prior to use in a patient. The term "terminally heat sterilized" or "heat sterilized" as used herein refers to the process involving heating a solution to about 120° C. for 15 minutes under pressure, i.e., maintaining heat and pressure conditions for a period of time sufficient to kill all or substantially all bacteria and inactivate all or substantially all viruses in the solution. This procedure is normally performed in an autoclave, and is also known as "autoclaving". The purpose of heat sterilization is to kill possible infectious agents present in the solution. Infectious agents are known to tolerate temperatures up to 100° C. It is generally considered by the art that heating a solution under pressure to 120° C. for about 15 minutes is sufficient to insure sterility.

The solutions also include an oncotic agent. The oncotic agent is composed of molecules whose size is sufficient to prevent its loss from the circulation by readily traversing the fenestrations of the capillary bed into the interstitial spaces of the tissues of the body. As a group, oncotic agents are exemplified by blood plasma expanders. Compounds finding use as oncotic agents in the subject invention may be natural or synthetic, and will usually be polymeric compositions having an average molecular weight of at least about 40,000, usually at least about 100,000 and more usually at least about 200,000, where oncotic agents having a molecular weight of 300,000 or higher may find use. Examples of oncotic agents suitable for use in the solution of the present invention include proteinaceous compounds, such as albumin, e.g. human serum albumin, and cross-linked or high molecular weight hemoglobin, polysaccharides such as glucan polymers, and the like; organic polymers, e.g. PVP, PEG, etc.; and the like; where non-antigenic polysaccharides are preferred;

Polysaccharides that find use as oncotic agents in the subject solutions include hydroxyethyl starches, hydroxymethyl alpha (1→4) or (1→6) polymers, D-glucose polymers, e.g. dextrans having an alpha (1→6) linkage, cyclodextrins, hydroxypropylstarches, hydroxyacetylstarches, and the like.

Hydroxyethyl starches are of particular interest for certain embodiments of the subject invention. The average molecular weight of hydroxyethyl starches finding use in the subject invention may range from 10,000 d to 1,000,000 d or higher, where the molecular weight will typically range from about 40,000 d to 1,000,000 d, usually from about 100,000 to 900,000, and more usually from about 200,000 to 800,000. Preferred are compositions in which the average molecular weight of the hydroxyethyl starch oncotic agent ranges from about 50,000 d to 1,000,000 d, usually from about 100,000 to 900,000 and more usually from about 200,000 to 800,000. The degree of substitution will range from about 4 to 10, where in certain embodiments, the degree of substitution will range from 6 to 10 or 7 to 10, in other embodiments will range from 4 to 6 or 4 to 5, and in other embodiments will range from 6 to 8 or 6 to 7. Therefore, one class of preferred solutions will comprise a hydroxyethyl starch with between about 6 and 7 hydroxyethyl groups for every 10 glucose units. Another class of preferred solutions will comprise between about 4 and 6 or 4 and 5 hydroxyethyl groups for every 10 glucose units. Yet another class of preferred solutions will comprise between about 7 and 8 hydroxyethyl groups for every 10 glucose units.

A particularly preferred oncotic agent is Hetastarch (McGaw, Inc.), an artificial colloid derived from a waxy starch composed almost entirely of amylopectin with hydroxyethyl ether groups introduced into the alpha (1→4) linked glucose units and having a molar substitution of about 0.7 hydroxyethyl groups/glucose unit. The colloid properties of a 6% solution (wt/wt) of Hetastarch approximates that of human serum albumin.

Another particularly preferred oncotic agent is Pentastarch, which has a molar substitution of about 0.5 hydroxyethyl groups/glucose unit with a range of from about 0.4 to 0.5 and an average molecular weight range (as measured by the HPSEC method as reported in PDR 1996) of from about 150,000 to 350,000 d, with 80% between 10,000 and 2,000,000 d.

Another particularly preferred oncotic agent is "Hexastarch," which has a molar substitution of about 0.6 to 0.7 (e.g. 0.64) hydroxyethylgroups/glucose unit and an average molecular weight of about 220,000.

In certain embodiments, the hydroxyethyl starch will be a select fraction of the initial hydroxyethyl starch source, particularly a select size fraction, where generally the fraction will be a fraction in which substantially none of the polymeric molecules has a molecular weight greater than about 1,000,000 daltons or less than about 50,000 daltons, where by substantially none is meant less than 10%, typically less than 5% of the polymeric molecules are above the upper threshold or below the lower threshold. As such the fractionated oncotic agents have reduced polydispersity. Conventional fractionation means may be used to prepare such fractions.

The concentration of oncotic agent in the solution is sufficient to achieve colloid osmotic pressure approximating that of normal human serum, about 15 to 40 mm Hg, and in certain embodiments about 28 mm Hg. Generally, the amount of oncotic agent in the solution will range from about 0.5 to 30%, usually from about 1 to 25% and more usually from about 2 to 8%. Where the oncotic agent is a hydroxyethyl starch, the amount present in the solution will range from about 1 to 30%, usually from about 2 to 15% and more usually from about 4 to 8%.

In one aspect of the invention, the solution contains two or more oncotic agents with differential clearance rates. The solutions of the present invention having two or more oncotic agents with differential clearance rates provide additional advantages in restoring blood oncotic pressure in a hypovolemic subject over an extended period of time, while encouraging the subject's own production of plasma proteins. Artificial oncotic agents with relatively slow clearance rates include high molecular weight Hetastarch (molecular weight 300,000–1,000,000) and dextran 70, measured to have intravascular persistence rates of 6 hours (Messmer (1989) Bodensee Symposium on Microcirculation (Hammersen & Messmer, eds.), Karger, N.Y., pg. 59). Artificial oncotic agents with relatively fast clearance rates include low and medium molecular weight hydroxyethyl starches with lower degrees of substitution, e.g. about 0.40 to 0.65, and dextran 40, having intravascular persistence rates of 2–3 hours (Messmer (1989) supra).

The solution may further comprise one or more different optional agents which may be included in the solution to make the solution suited for a particular application. One optional agent that may be included, and usually is included, is sugar. The sugar will generally be a hexose sugar, such as glucose, fructose and galactose, of which glucose is preferred. In the preferred embodiment of the invention nutritive hexose sugars are used and a mixture of sugars can be used. The sugar is typically, though not necessarily, present in the solution in a physiological amount. By the term "physiological amount" or "physiological levels" is meant the concentration of sugar is in a range between 2 mM and 50 mM with concentration of glucose of 5 mM being preferred. At times, it is desirable to increase the concentration of hexose sugar in order to lower fluid retention in the tissues of a subject. Thus the range of hexose sugar may be expanded up to about 50 mM or even above, but usually not above 60 and more usually not above 55 mM, if necessary to prevent or limit edema in the subject under treatment, except where the agent is present as a cryoprotective agent, as described in greater detail below.

In certain embodiments, the solutions of the present invention may include a blood clotting factor able to accelerate or promote the formation of a blood clot. Preferred blood clotting factors for use in the solution of the invention include vitamin K, Factors I, II, V, VII, VIII, VIIIC, IX, X, XI, XII, XIII, protein C, von Willebrand factor, Fitzgerald factor, Fletcher factor, and a proteinase inhibitor. The concentration of the blood clotting factor is determined by one skilled in the art depending on the specific circumstances of treatment. For example, generally when vitamin K is administered, its concentration will be sufficient to deliver 5–10 mg to the patient.

Fluid Blood Composition

The second essential fluid composition that is employed in the subject methods is the fluid blood composition. By fluid blood composition is meant a fluid medium that is whole blood or derived from whole blood, such as an aqueous suspension of one or more of red blood cells, platelets, plasma protein, albumin purified from whole blood, whole plasma or fractions thereof, e.g. fibrin free plasma, and the like. Importantly, because of the constituent make up of the fluid blood composition, the fluid blood composition is not thermally sterilizable, as such thermal sterilization irreversibly damages one or more of the constituents of the fluid blood composition. In many embodiments, the fluid blood composition comprises one or more blood derived cellular components, where cellular components includes both whole cells and fragments, portions or derivatives thereof, such as red blood cells, platelets, and the like. The preparation of such components from whole blood is well known to those of skill in the art and any convenient methodology for such preparation may be employed. The naturally occurring blood components are present in a physiologically acceptable solution, such as the plasma-like solution described above. Fluid blood compositions that find use in the subject invention also include whole blood. The blood components of the fluid blood composition may comprise donor components or components previously harvested from the subject undergoing the procedure in which the composition is employed. For example, where the fluid blood composition is whole blood, the whole may be the patient's blood (having been previously harvested from the patient) or donor blood. In addition, the components may be synthetically produced, e.g. recombinant albumin.

Optional Fluid Compositions

In addition to the above two fluid compositions, the subject methods may further employ one or more of the following optional solutions, where the following optional solutions are derivatives of the basic non-naturally occurring plasma-like solution described above.

Bicarbonate Plasma-Like Solution

Bicarbonate plasma-like solutions of the subject invention are synthetic plasma-like solutions, as described above, that further include bicarbonate ion. Any convenient source of bicarbonate ion may be included in the synthetic plasma-like solution in order to obtain the subject carbonate plasma-like solution, where the bicarbonate solutions usually include sodium bicarbonate ($NaHCO_3$). The concentration of $NaHCO_3$ ranges from about 0.1 mM to 40 mM, usually from about 0.5 mM to 30 mM, and more usually from about 1 mM to 10 mM.

Bioenergetic or Supercharger Solutions

Also of interest are variations of the subject plasma-like solutions which include elevated levels of potassium and magnesium electrolytes (known as "bioenergetic" or "supercharger solutions"). By elevated levels is meant a potassium ion concentration in an amount ranging from about 50 mM to 3.0 M, usually from about 200 mM to 2.5 M, and more usually from about 1.0 to 2.5 M, and a magnesium ion concentration of from about 40 mM to 1.0 M, usually from about 0.1 to 0.9 M and more usually from about 0.3 to 0.7 M. Theses solutions may further comprise, in certain embodiments, bicarbonate, where the bicarbonate will be present in amounts ranging from about 0.1 to 40 mM, usually from about 0.5 to 30 mM and more usually from about 1 to 10 mM.

Oxygen Carrying Solutions

Also of interest are the subject synthetic plasma-like solutions that have been modified to include oxygen carrying compounds. Generally, the oxygen-carrying compound or component is present in a concentration sufficiently low so as not to be toxic to the subject. The oxygen carrying component will usually be present in a sufficient amount to deliver enhanced oxygen to the tissues of a subject without resulting in toxicity to the subject. A "sufficient amount" of an oxygen-carrying component is an amount allowing a resting subject with an unimpaired circulation and physiology to survive and recover from trauma, illness or injury. In normal humans at normal body temperature, this is at least 5–6 ml $O_2$/100 ml of intravascular fluid. Oxygen-carrying components include hemoglobin extracted from human and non-human sources, recombinant hemoglobin, hemocyanin, chlorocruorin and hemerythrin, and other naturally occurring respiratory pigments extracted from natural sources or made by recombinant DNA or in vitro methods. These compounds may be modified by a number of means known to the art, including by chemical crosslinking or covalent bonding to polyethylene glycol group(s). When the oxygen-carrying component is hemoglobin, it is preferably present in the concentration range of between about 20–200 g/l.

Instead of, or in addition to, the presence of the oxygen carrying component, the plasma-like solution may be treated in a manner which increase the dissolved $O_2$ content of the solution to a desirable level, where desirable levels generally range from about 3 to 60 ml/dl, usually from about 3 to 40 ml/dl and more usually from about 4 to 25 ml/dl. A variety of different technologies are available for oxygenating solutions, where such technologies include: pressurizing with hyperbaric oxygen; bubble oxygenation; passing the solution through an oxygenating membrane, such as the those sold by Terumo Corporation (Japan); and the like.

Cryogenic Solutions

Cryogenic solutions are also provided by the subject invention. Any of the above synthetic plasma-like solutions may be modified to include one or more cryoprotective agents to produce a cryogenic solution of the invention, where by cryoprotective agent is meant any agent that preserves the structural integrity of tissue under hypothermic, e.g. sub-zero, conditions, where in certain embodiments the cryoprotective agent will be an agent that modulates or influences, at least to a partial extent, the ordered crystal arrangement of water molecules. Cryoprotective agents of interest include: alcohols, particularly low molecular weight aliphatic alcohols, usually $C_1$ to $C_6$ alcohols, more usually $C_1$ to $C_4$ alcohols, such as methanol, ethanol, and the like; polyols, including linear, branched and cyclic polyols, usually low molecular weight aliphatic polyols, including diols, triols, and other polyols, such as sugars (described in greater detail below) where polyols of particular interest include diols, such as ethylenediol, propanediol, butanediol, triols, e.g. glycerol, and the like; sugars, including erythrose, threose, ribose, arabinose, xylose, lyxose, allose, atrose, glucose, mannose, gulose, idose, galactose, talose, erythrulose, ribulose, xylulose, psicose, fructose, sorbose, tagatose and disaccharides, e.g. sucrose, lactose and maltose, where glucose is particularly preferred; other agents such as timethylamine, trimethylamine oxide (TMAO), DMSO, urea, formamide, dimethylformamide and the like; clathrates, silicon comprising agents, such as silanes and the like, fluorocarbon compounds and derivatives thereof; etc; where the cryoprotective agent may be forced into solution by pressure and/or a suitable surfactant agent may be employed, where such surfactant agents are known to those of skill in the art. Such agents will typically be present in amounts sufficient to provide the desired cryoprotective effect, where the particular amount of the agent will depend on the particular agent employed. When the agent is a polyol, e.g. a diol, it will generally be present in amounts ranging from about 0.2 to 1 M or 0 to 30%. With respect to propanediol, in particular a range of 0.2 M to 0.6 M is preferred and a concentration of about 0.4 M propanediol is most preferred. 1,2 propanediol is preferred as the adduct to the solution used for low temperature organ and donor preservation according to the invention, although 1,3 propanediol may be used. For TMAO, TMAO will be present in the solution in a final concentration in a range between 0.2 M and 7M. When glycerol is employed, it will be present in a concentration ranging from about 0 to 40%, usually from about 5 to 30%, and more usually 5 to 20%. When DMSO is employed, it will be present in amounts ranging from about 0 to 40%, usually from about 5 to 30%, and more usually from about 5 to 20%. When a sugar is employed (particularly glucose), the sugar ranges between about 0.6 M to about 1.4 M, with 1.0 M being preferred for certain embodiments.

METHODS OF PREPARING THE FLUID COMPOSITIONS

In preparing the subject solutions and fluid compositions, the various constituents may be combined at substantially the same time, or added sequentially, as may be convenient. In most situations, the non-naturally occurring plasma-like solutions may be terminally heat sterilized as described above. As also described above, the solutions may further comprise agents that should not be terminally heat sterilized, such as a source of bicarbonate, where the bicarbonate participates in the dynamic buffering system. In such instances, the sodium bicarbonate will be added as a sterile solution to a pre-autoclaved "base solution." Similarly, when it is desirable to add a blood clotting factor or oxygen-carrying component, the blood clotting factor or oxygen-carrying component is added as a sterile solution to the autoclaved base solution.

For purposes of description of the invention, the mixture according to the invention has been discussed and will continue to be discussed in terms of an aqueous solution. From the following description of the invention it is expected that one of ordinary skill in the art would be enabled to provide the mixture as a dry mixture which can then be later hydrated.

METHODS OF USE

The above described solutions find use in methods of perfusing a subject. The term "subject" is used broadly to refer to any biological entity having a circulatory system, and therefore includes: whole organisms, e.g. mammals, including dogs, cats, rodents, cows, horses, and humans; as well as derivatives of such organisms, such as a tissues or organs, e.g. the heart, liver, kidney, etc.

In practicing the subject methods, at least two fluid compositions are sequentially administered to the subject, or derivative thereof. The first fluid composition is the plasma-like solution, described above. The second fluid composition is the fluid blood composition. By sequentially administered is meant that the first fluid composition is administered to the subject prior to the second fluid composition. The subject invention also encompasses those methods in which two or more quantities of the first fluid composition are administered and/or two or more quantities of the second type of fluid composition are administered. Thus, in the broadest sense the subject methods are directed to methods in which at least one administration of the first type of fluid composition is administered followed by at least one administration of the second type of fluid composition.

In many embodiments, one or more additional fluid compositions, e.g. the bicarbonate plasma-like solution, the cryogenic solution, the supercharger solution etc., are administered to the host. These additional fluid compositions may be administered at any time prior to, between or after the first and second fluid compositions, depending on the particular method being performed. In certain embodiments, the following sequential order of fluid compositions is administered to the subject: (1) plasma-like solution; (2) bicarbonate plasma-like solution; (3) bioenergetic solution; (4) bicarbonate plasma-like solution; and (5) fluid blood composition. In yet other embodiments, the following order of fluid compositions is administered to the subject: (1) plasma-like solution; (2) bicarbonate plasma-like solution; (3) bioenergetic solution; (4) cryogenic solution; (5) bicarbonate plasma-like solution; and (6) fluid blood composition.

In a class of preferred embodiments, administration of the fluid blood composition is followed by administration of an additional volume of the non-naturally occurring plasma-like solution or a derivative thereof, e.g. the plasma-like solution; the bicarbonate plasma-like solution; the bioenergetic solution; the cryogenic solution; etc.

In general, the fluid compositions according to the invention are administered using an intravenous line using a gravity feed line or a pumped circulating device such as a centrifugal pump, roller pump, peristaltic pump or other known and available circulatory pump. When employed, the circulating device is connected to the subject via cannulae inserted surgically into appropriate veins and arteries. For example, when the solution is administered to a chilled subject, it is generally administered via an arterial cannula and removed from the subject via a venous cannula and discarded, stored or circulated.

Depending on the particular method being performed and condition being treated, the subject methods may further include a step in which the temperature of the subject is modulated, e.g. raised or lowered from ambient temperature. In many embodiments, the temperature of the subject is lowered for at least a portion of the treatment process, i.e. the process in which the at least two fluid compositions are administered to the subject. Where the temperature of the subject is lowered, the temperature will generally be lowered to at least about 32, usually at least about 20 and more usually at least about 5° C., where the temperature may be lowered to −80° C. or lower, but will generally not be lowered to below −196° C. The temperature of the subject may be modulated using any convenient protocol, such as the use of temperature controlled rooms, warming or cooling blankets, perfusion with chilled or warmed solutions, immersion in cooling or warming fluids, etc.

Alternatively or in addition, the pressure of the subject may be modulated. As such, the subject may be pressurized, i.e. placed in a hyperbaric environment, for at least a portion of the subject methods. In the hyperbaric environment, the pressure is typically at least about 1.5 atm, and usually at least about 2.0 atm, where the pressure may be as high as 200 atm or higher, but will generally not exceed about 10,000 atm, usually will not exceed about 5000 atm more usually will not exceed about 2500 atm. The hyperbaric environment may be provided using any convenient technology. See e.g. U.S. Pat. Nos. 5,738,093; 5,678,722; 5,678,543; 5,398,678; 5,109,837; 5,060,644; 4,974,829; 4,837,390; 4,727,870; 4,655,048; 4,633,859; the disclosures of which are herein incorporated by reference. For example, a thick walled chamber pressurized with a gaseous medium, e.g. helium, argon, krypton, neon, may be employed to provide the hyperbaric environment.

The subject methods in which a subject is sequentially perfused with at least a synthetic plasma-like solution and a fluid blood composition find use in a variety of different applications, where such applications include: hypothermic surgical applications, hyperbaric surgical applications, organ or organism preservation, and the like. The following applications are representative of applications in which the subject methods find use.

One type of application in which the subject methods find use is hypothermic surgical applications, such as hypothermic cardiac surgery in which a cardiopulmonary bypass device is employed. In such methods, the subject is prepared for surgery in accordance with standard procedures. The subject is connected to the cardiopulmonary bypass machine according to the accepted protocol which depends on the particular machine being employed. A variety of different cardiopulmonary bypass machines, as well as protocols for their use, are known to those of skill in the art and include those described in: U.S. Pat. Nos. 5,827,220; 5,8209579; 5,800,375; 5,785,686; 5,688,245; 5,643,921; 5,478,309; 5,437,601; 5,383,854; 5,383,839; 5,334,136; 5,308,320; 5,300,015; 5,254,097; 5,158,539; 5,011,469; 4,808,163; 4,804,365; 4,690,002; 4,553,532; 4,398,872; 4,293,961; the disclosures of which are herein incorporated by reference. In preparing for surgery, a quantity of the synthetic plasma-like solution of the invention is administered to the subject as needed to prevent and/or treat hypovolemia during the preparation process, e.g. the instrumentation and cannulation of the subject; connection of the subject to the cardiopulmonary bypass device, etc. Generally, the amount of plasma-like solution that is administered ranges from about 0.25 to 10 l, usually from about 0.50 to 5.0 l and more usually from about 1.0 to 3.0 l.

Following preparation of the patient and completion of the circuit with the cardiopulmonary bypass, the sodium bicarbonate solution (as described above) is introduced into the circuit in a manner sufficient to replace substantially all of the patients blood from the patient's circulatory system. Substantially all of the patient's blood is considered to have been removed from the patient when the hematocrit of the patient falls below about 15%, usually below about 7% and more usually below about 3%.

Once substantially all of the patient's blood has been replaced with the bicarbonate priming solution, the temperature of the patient is cooled and a quantity of concentrated KCl solution is introduced into the circuit in a manner sufficient to achieve cardiac arrest. The subject or patient is cooled to a temperature of from about 28 to 1° C., usually from about 8 to 2° C. The concentrated KCl solution has a concentration sufficient to increase the potassium ion concentration in the fluid present in the subject's circulatory system to a value ranging from about 5 to 300 mM, usually from about 6 to 50 mM. As such, the concentration of the KCl solution ranges from about 0.3 to 3M, usually from about 0.5 to 2.8 M and more usually from about 1.5 to 2.5 M. The KCl solution may be made up of solely KCl and purified water, or may comprise one or more additional components, such as magnesium, bicarbonate, lactate, and the like. The amount of concentrated KCl solution that is introduced into the circuit is generally at least about 2 ml, usually at least about 10 ml and more usually at least about 50 ml, where the amount may be as high as 400 ml or higher, but will typically not exceed about 1 l and usually will not exceed about 500 ml.

Following introduction of the concentrated KCl solution, the temperature of the host or subject is lowered to the temperature desired for surgery, e.g. to a temperature between about 30 and 0° C., usually between about 25 and 1° C. and more usually between about 10 and 2° C., often by the addition of one or more liters of bicarbonate solution. Just prior to circulatory arrest surgery (i.e. where the heart has stopped beating), the bioenergetic solution is introduced. The amount of bioenergetic solution introduced is at least about 1 ml, usually at least about 100 ml, and more usually at least about 500 ml, where the amount maybe as high as 4 l or higher, but will typically not exceed about 3 l and usually will not exceed about 2 l.

The above steps result in a subject under cardiac arrest and profound hypothermia, where the temperature of the subject ranges from about 30 to 2° C., usually from about 10 to 2° C. These conditions are maintained during the particular hypothermic surgical procedure being performed.

Following completion of the surgical procedure, the circuit is flushed with fresh biocarbonate plasma-like soluttion and the subject is gradually warmed to a temperature ranging from about 0 to 20° C., usually from about 2 to 12° C. One or more additional flushes with bicarbonate solution may be employed. Once the temperature of the subject reaches 4 to 28° C., the fluid blood composition, e.g. whole blood, is introduced into the circuit in a manner sufficient to raise the hematocrit to where cardiac function may be restored, where cardiac function may, be restored via mechanical means, electrical means, pharmaceutical means, spontaneous defibrillation, and the like, as is known to those of skill in the art. For example, whole blood is infused until the subject achieves an acceptable hematocrit, generally exceeding hematocrits of about 28%. When an acceptable hematocrit is achieved and perfusion is discontinued, the subject is revived after closure of surgical wounds using conventional procedures.

The subject methods also find use in cryogenic preservation applications, in which an organism or derivative thereof, either living or non-living, is to be preserved for an extended period of time. In such methods, the subject or derivative thereof is first cooled to a hypothermic temperature ranging from about 35 to 0° C. usually from about 30 to 5° C. and more usually from about 10 to 0° C., where in certain embodiments the hypothermic temperature ranges from about 20 to 0° C. and usually 12 to 0° C., using any convenient protocol, e.g. cooling blankets, perfusion with cooled fluids, etc. During this initial cooling process, the subject is perfused with the synthetic plasma like solution as described above, such that substantially all of the subject's blood is removed and replaced with the synthetic-plasma like solution.

Following cooling of the subject and replacement of the subject's blood with the synthetic plasma-like solution, which may or may not be the bicarbonate plasma-like solution, the hypothermic subject is moved to a hyperbaric environment, e.g. a walled chamber of sufficient strength to withstand the pressures to be produced inside the chamber. For example, a thick-walled chamber made of a suitably strong material and appropriate construction, e.g. cryogenic steels and the like, may be employed. The chamber may be equipped with heating and cooling means, as well as means for monitoring the subject and means for introducing and removing fluids from the circulatory system of the subject present in the chamber. The subject is pressurized by introducing a sufficient quantity of a suitable gas into the chamber. A variety of gases may be employed, including helium, as well as other noble gases, such as argon, krypton, or neon. The subject is then pressurized to the desired hyperbaric pressure, which generally ranges from about 2 to 10,000 atm, usually from about 100 to 5000 atm and more usually from about 300 to 3000 atm.

Of particular interest is the subjection of the patient to conditions sufficient for ICE3 formation. Under such conditions, the temperature of the subject is reduced to a value ranging from about −1 to −200, usually from about −5 to −40 and more usually from about −15 to −25° C. The pressure of the subject typically ranges from about 10 to 5000, usually from about 500 to 3000 atm.

In certain embodiments of the above preservation procedures, it is desirable to introduce a cryogenic, solution (as described above) into the subject. Where a cryogenic solution is employed, the temperature to which the subject is lowered for storage may range from about −2 to −270° C., usually from about −40 to −250° C. and more usually from about −60 to −200° C.

Using the above protocols, the subject may be stored for indefinite periods of time. Generally, the subject will be maintained in a pressurized and hypothermic state during storage. However, in certain embodiments, it may be possible to depressurize the subject where the subject is preserved in a metastable state.

Following storage of the subject, the subject may be gradually warmed and depressurized in a manner that provides for minimal tissue damage. At some point during this process, generally when the temperature is between about 8 and 28° C. and the pressure is between about 1 and 5 atm, the subject is perfused with the fluid blood composition, e.g. whole blood. The subject may or may not be revived.

KITS

Also provided by the subject invention are kits for use in performing the subject methods. The subject kits at least include the synthetic plasma-like solution in combination with instructions for practicing the subject methods. The amount of synthetic plasma-like solution that is included in the kits may vary, but will generally range from about 0.5 to 1000 l, usually from about 1 to 300 l and more usually from about 1 to 100 l. The solution may be present in any convenient container or package, such as a flexible polymeric bag, and the like. The instructions for practicing the subject method may be present on one or more of a package insert, the containing or packaging of the device. The subject kits may further comprise one or more additional fluid compositions, depending on the particular method to be performed. These additional fluid compositions include: a concentrated KCl solution, a bicarbonate solution, a bioenergetic solution, a heta freeze solution and the like, where the kits may include one or more of these various solutions pre-made or may include components that can be combined at the time of use with the provided synthetic plasma-like solution in order to prepare the solution of interest. In addition, the subject kits may further include the fluid blood composition that is employed in the methods, particularly where the subject's own blood is to be discarded and replaced with donor blood or blood components.

SYSTEMS

Also provided are systems for use in performing the subject methods. The subject systems are specifically designed to optimally sequentially deliver the plasma-like solution and fluid blood composition to a subject under controlled temperature and pressure conditions. As such, the subject systems may include: circuitry for establishing fluid communication with the circulatory system of the host; oxygenators; pumps to move the subject fluid compositions through the circulatory system of the host; heat exchangers, dialysis circuits; computers and monitors to collect, store, process and display data, e.g. pressure and temperature; means for establishing a hyperbaric environment, e.g. a tent or chamber for delivering hyperbaric oxygen to the subject; means for controlling the temperature of the subject, e.g. warming and cooling blankets; and the like.

The following examples are offered by way of illustration and not by way of limitation.

EXPERIMENTAL

| | | | |
|---|---|---|---|
| I. | Fluid Compositions: | | |
| A | Plasma-Like Solution | | |
| | High Molecular Weight Hetastarch | | |
| | (average molecular wt. of 350,000–900,000) | | 1 to 10% |
| | Ca++ | | 1–6 mM |
| | K+ | | 1–5 mM |
| | Mg++ | | 0–10 mM |
| | lactate | | 1–40 mM |
| | glucose | | 0–50 mM |
| B. | Bicarbonate Plasma–Like Solution | | |
| | High Molecular Weight Hetastarch | | |
| | (average molecular wt. of 350,000–900,000) | | 1 to 10% |
| | Ca++ | | 1–6 mM |
| | K+ | | 1–5 mM |
| | Mg++ | | 0–10 mM |
| | lactate | | 1–40 mM |
| | glucose | | 0–50 mM |
| | bicarbonate | | 5–10 mM |
| C. | Bioenergetic Solution (please provide composition) | | |
| | K+ | | 100 to 3000 mM |
| | Mg++ | | 30 to 1000 mM |
| D. | Cryoprotective Solutions | | |
| 1. | High Molecular Weight Hetastarch | | |
| | (average molecular wt. of 350,000–900,000) | | 1 to 10% |
| | Ca++ | | 1–6 mM |
| | K+ | | 1–5 mM |
| | Mg++ | | 0–10 mM |
| | lactate | | 1–40 mM |
| | glucose | | 0–50 mM |
| | bicarbonate | | 5–10 mM |
| | glycerol | | 10–20% |
| 2. | High Molecular Weight Hetastarch | | |
| | (average molecular wt. of 350,000–900,000) | | 1 to 10% |
| | Ca++ | | 1–6 mM |
| | K+ | | 1–5 mM |
| | Mg++ | | 0–10 mM |
| | lactate | | 1–40 mM |
| | bicarbonate | | 5–10 mM |
| | glycerol | | 10–20% |
| 3. | High Molecular Weight Hetastarch | | |
| | (average molecular wt. of 350,000–900,000) | | 1 to 10% |
| | Ca++ | | 1–6 mM |
| | K+ | | 1–5 mM |
| | Mg++ | | 0–10 mM |
| | lactate | | 1–40 mM |
| | glucose | | 0–50 mM |
| | bicarbonate | | 5–10 mM |

-continued

| EXPERIMENTAL | |
|---|---|
| glycerol | 5–15% |
| DMSO | 5–15% |

Hypothermic Cardiovascular Surgery

The patient is anesthetized, instrumented and catheterized. A portion of the patient's blood volume (I liter), is collected and replaced with a liter of a Plasma-Like Solution. The patient's chest is then opened. The volume of blood lost in these procedures is replaced first with collected blood, and then with Plasma-Like Solution. The aorta and the vena cava are cannulated for cardiopulmonary bypass. The patient's circulation is connected to the bypass circuit (filled with a Bicarbonate Plasma-Like Solution) which contains a blood pump, an oxygenator and a heat exchanger. The patient's body temperature is then lowered to 14° C. and the circulating blood is replaced with the Bicarbonate Plasma-Like Solution. This is continued until the hematocrit approaches 1%. During this blood volume replacement, the remainder of the patient's blood is collected for use during warming, followed by the intra-arterial injection of 100 ml of a 2 mEq/ml KCl solution to arrest cardiac fibrillation. After virtually all the patient's blood is replaced with a Bicarbonate Plasma-Like Solution, the body temperature is lowered to approximately 4° C., and 500 ml of the Bioenergetic Solution (375 ml of a 2 mEq/ml KCl solution and 125 ml of a 50% $MgSO_4.7H_2O$ solution) is introduced intra-arterially and circulated for 4 minutes.

Following the completion of surgery, the circuit is cleared of the Bicarbonate Plasma-Like Solution to which was added the Bioenergetic Solution. The patient is then warmed, and flushing is then continued with enough Bicarbonate Plasma-Like Solution to lower the blood plasma K+ concentration to below 6 mEq/L. At 14° C., diluted blood initially collected from the patient is returned, and as the patient becomes warmer, more blood is added. When the patient is removed from bypass, the remainder of the blood cells in the circuit is returned to the patient, as well as any of the patient's remaining whole blood collected at the beginning of the procedure. The patient is then warmed to normal body temperature, all incisions are closed, and the patient maintained on anesthetics and a ventilator until awakened the next day.

Cryogenic Preservation

A 50 g hamster is injected with ketamine and placed in crushed ice. When its body temperature sinks to 12° C., the hamster is then placed underneath a stereo microscope, instrumented, cannulated, ventilated with 100% $O_2$, chilled to 1° C. Its blood is replaced with 4 ml of the Bicarbonate Plasma-Like Solution, then 4 ml of the Bioenergetic Solution and then with 10 ml Cryoprotective Solution 1. The hamster is placed in a thick walled chamber and compressed to 1500 atm. of helium, while its temperature is lowered stepwise to −20° C. The temperature is then lowered to −196° C., and the hamster slowly depressurized. After storage at this temperature for 1 week, the hamster is re-pressurized to 1500 atm with helium. It is then warmed to −20° C., then slowly depressurized while warming to 1° C. The hamster is again perfused with the Bicarbonate Plasma-Like Solution, then warmed while being perfused with whole blood. The animal is ventilated with 100% $O_2$, brought to normal temperature.

59 patients undergoing major elective surgery for gastrointestinal, urological, gyecological and orthopedic pathology were intraoperatively infused with intraveneous Plasma Like Solution in response to loss in blood pressure. Of these patients, 31 lost sufficient amounts of blood to require transfusion with packed red blood cells following infusion with the Plasma-Like Solution. The average amount of Plasma-Like Solution that was infused into these patients was approximately 2.1 l. The average amount of packed red blood cells that was transfused was approximately 1 l. In a number of patients, additional Plasma-Like Solution was then infused, followed by transfusion of an additional amount of packed red blood cells. All patients successfully recovered from their operations and there were no serious related adverse events related to the use of the Plasma Like Solution.

It is evident from the above results and discussion that the subject invention provides for methods of perfusion of a subject that find use in a variety of different applications. Use of the subject methods results in better outcomes in a variety of different applications, including hypothermic surgery, cryogenic preservation, and the like.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a subject for hypovolemia, said method comprising: administering to said subject:
    (a) a conventional biological buffer free non-naturally occurring plasma-like solution comprising:
        (i) electrolytes;
        (ii) an oncotic agent;
        (iii) and a dynamic buffering system; and
    (b) a fluid blood composition,
wherein said subject is treated for hypovolemia by said administration of said conventional biological buffer free non-naturally occurring plasma-like solution and said fluid blood composition.

2. The method according to claim 1, wherein said electrolytes include: $Na^+$, $Mg^{2+}$, $Ca^{2+}$, and $Cl^-$.

3. The method according to claim 2, wherein said non-naturally occurring plasma-like solution further includes $K^+$.

4. The method according to claim 1, wherein said oncotic agent is a polymer.

5. The method according to claim 1, wherein said dynamic buffering system comprises an organic carboxylic acid, salt or ester thereof.

6. The method according to claim 1, wherein said non-naturally occurring plasma-like solution further includes a sugar selected from the group consisting of monosaccharides and disaccharides.

7. The method according to claim 1, wherein said fluid blood composition is whole blood or a derivative thereof.

8. The method according to claim 7, wherein said fluid blood composition is not thermally sterilizable.

9. The method according to claim 1, wherein said method further comprises the introduction of at least one additional fluid composition.

10. The method according to claim 1, wherein said method further comprises reducing the temperature of said subject.

11. The method according to claim 1, wherein said method further comprises placing said subject into a hyperbaric environment.

* * * * *